United States Patent [19]

Gysling et al.

[11] 4,239,846
[45] Dec. 16, 1980

[54] TELLURIUM (IV) COMPOUNDS AND COMPOSITIONS

[75] Inventors: Henry J. Gysling; Sylvia A. Gardner, both of Rochester, N.Y.

[73] Assignee: Eastman Kodak Company, Rochester, N.Y.

[21] Appl. No.: 894,863

[22] Filed: Apr. 10, 1978

[51] Int. Cl.$^3$ .......................... G03C 5/54; G03C 1/00; G03C 5/24; G03C 1/02
[52] U.S. Cl. ................................... 430/202; 430/231; 430/227; 430/464; 430/477; 430/495; 430/616; 430/617; 260/333; 260/550; 106/1.22; 546/314; 546/255; 568/734; 568/734; 568/716; 549/28; 564/436; 564/453
[58] Field of Search .......... 96/29 R, 76 R, 88, 48 PD, 96/48 HD, 88, 114.1; 106/1.22; 430/231, 227, 464, 477, 616, 617, 202, 495

[56] References Cited

U.S. PATENT DOCUMENTS 4,097,281  6/1978  Gardner et al. .................. 96/48 HD

FOREIGN PATENT DOCUMENTS 2239702  2/1975  France ......................... 96/88
135540  11/1976  Japan .......................... 96/88
1484891  9/1977  United Kingdom ................. 96/48 HD Primary Examiner—Won H. Louie, Jr.
Attorney, Agent, or Firm—J. Jeffrey Hawley

[57] ABSTRACT

Disclosed are tellurium (IV) compounds represented by the formula:

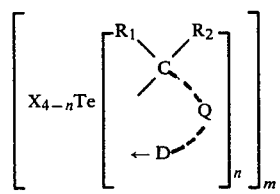

wherein:

D is a Lewis base function containing a group VA or VIA donor atom;

Q represents the atoms necessary to complete a 5- or 6-membered ring, when taken together with C, D and Te, when m is 1 and represents the atoms linking C and D when m is greater than 1;

$R_1$ and $R_2$ are independently selected from the group consisting of hydrogen, alkyl and aryl;

X is an anion;

n is 1 or 2; and m is an integer from 1 to 500.

These compounds are useful in an image-forming combination comprising the described Te(IV) compound and a reducing agent. The image-forming combination is useful in a variety of materials, including a dry amplification element.

26 Claims, 2 Drawing Figures

TELLURIUM (IV) COMPOUNDS AND COMPOSITIONS

BACKGROUND OF THE INVENTION

1. Field of the Invention

This invention relates to tellurium (IV) [hereinafter referred to as Te(IV)] compounds and their use in photographic elements and processes. More particularly, the Te(IV) compounds are useful in various photographic elements that are processed with heat.

2. Description Relative to the Prior Art

It is known to provide an image in an imaging material containing metal compounds. These materials can be useful in what are described as photographic materials for dry processing with heat, heat-developable photographic materials or photothermographic materials. Such heat-developable photographic materials, after imagewise exposure to provide a developable latent image, are heated to provide a developed image without requiring processing solutions.

An image amplification step is an important factor in providing photographic materials, including photothermographic materials, having increased speed. In these materials, a latent image is generally formed by imagewise exposure of photosensitive material to suitable radiation. The resulting invisible or latent image formed is then used to catalyze the reduction of a material in a high oxidation state to a low oxidation state, thereby forming an image. In silver halide photographic materials, for example, exposure of photographic silver halide to light results in formation of silver nuclei, i.e., specks of silver metal, which then can catalyze the further reduction of silver halide in the presence of a reducing agent.

The use of tellurium compounds in imaging is known. For instance, it is known to produce negative tellurium images by disproportionation of tellurium dihalides. The images are formed in the presence of a processing liquid or solution. The liquid aids in the disproportionation reaction. The unexposed dihalides, however, are dark in color, causing poor discrimination between exposed and unexposed areas. Further, the tellurium dihalides are typically unstable in air and undergo light induced decomposition only when moistened with an organic solvent.

Other tellurium imaging materials are known which contain certain Te(IV) compounds wherein the tellurium is bonded directly to a carbon atom. These tellurium materials undergo what can be described as a unit quantum photoreduction to yield a tellurium (0) image. These materials and imaging processes do not involve a catalytic amplification of a latent image. That is, the tellurium (0) formed upon exposure does not catalyze the decomposition of other components or other reaction of the Te(IV) compounds. These processes and imaging materials are inherently photographically slow in speed and limited in usefulness because they do not employ an amplification reaction.

Useful imaging elements and processes using Te(IV) compounds are disclosed in copending commonly assigned U.S. Pat. Nos. 4,144,062 issued Mar. 13, 1979, and 4,152,155 issued May 1, 1979. In these applications, there are described certain imaging compositions comprising (1) a tellurium compound [which can be a Te(IV) compound] as an oxidizing agent, with (2) a reducing agent. This imaging combination can be useful in heat-developable photographic materials containing, for example, photographic silver halide or other sources of developable nuclei. Among the Te(IV) compounds described in those applications are compounds having the formula: $X_3TeR$, wherein R is alkyl or aryl, and X is an anion. While these compounds are particularly useful in solution processes, compounds of this general class, where R is alkyl, may be relatively unstable in air. On exposure to air for even a short period, some of these compounds tend to hydrolyze to a white gum. (See G. T. Morgan and O. C. Elvins, J. Chem. Soc., 2627 [1925]). It is readily apparent that this can severely limit the usefulness of these compounds in commercial elements and processes.

SUMMARY OF THE INVENTION

We have found a new class of Te(IV) compounds. In the new compounds of our invention, a tellurium atom is bonded to both a carbon atom and at least one Lewis base function incorporated within the same ligand. These compounds are more hydrolytically stable in air than are analogous Te(IV) compounds which have a Te-C bond, but wherein the tellurium is not bound to a Lewis base function in the ligand. Despite the increased stability of the compounds of the present invention, they are capable of catalytic decomposition in the presence of a physically developable catalyst.

The Te(IV) compounds of the present invention can be represented by the formula:

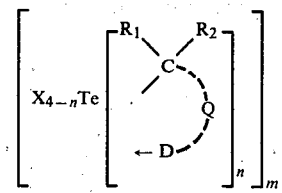

wherein:

D is a radical representing one or two Lewis base functions, each function containing a group VA or VIA donor atom and coordinated with a Te atom of the compound;

Q represents the atoms necessary to complete a 5- or 6-membered ring, when taken together with C, D and Te, or if m is greater than 1, represents only the atoms linking C and D, such as alkylene or arylene, and does not constitute the completion of a 5- or 6-membered ring;

$R_1$ and $R_2$ are independently selected from the group consisting of hydrogen, alkyl and aryl, and are preferably hydrogen;

X is an anion;

n is 1 or 2, preferably 1; and m is an integer from 1 to 500.

The Te(IV) compounds described above undergo catalytic reduction in the dry state in the presence of a physically developable catalyst to deposit tellurium (0). Thus, in another aspect of the invention, there is provided an image-forming combination comprising (i) a Te(IV) compound described above, and (ii) a reducing agent. The image-forming combination can be used in a variety of ways. For example, it can be included in a solution to provide a physical development bath. Alternatively, it can be coated on a support to provide an amplification element. In another embodiment, the Te(IV) compound and the reducing agent can be coated in reactive association with a photosensitive material salt to provide a photothermographic element.

The Te(IV) compounds of the present invention offer distinct advantages over known tellurium-containing compounds in that they can be prepared and incorporated in the various described compositions and elements without expensive precautions being taken to exclude moisture.

DETAILED DESCRIPTION OF THE INVENTION

In the compounds of the present invention, a tellurium atom is bound to a carbon and to a Lewis base function incorporated within the same ligand. The compounds of the present invention are not necessarily chelates in the classical sense. Classically, a chelate is a compound wherein a ligand coordinates to a metal ion through two or more group VA or VIA donor atoms. In the compounds of the present invention, a tellurium (IV) atom is bound in at least two positions to a ligand. At least one bond is to a carbon atom with the other bond or bonds being to a group VA or VIA donor atom.

The compounds of the present invention can be represented by the general formula:

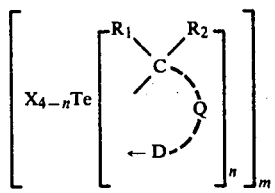

wherein:

n is 1 or 2; and m is 1 for intramolecular coordination or more than 1 for intermolecular coordination, and preferably is from 1 to 500.

Figure 1A:
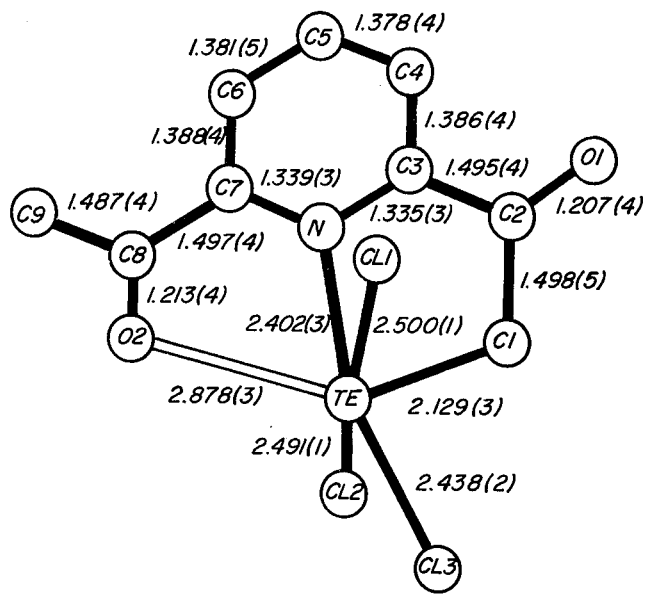
FIG. 1 is a representation of a compound of the present invention. The representation is derived from x-ray crystal analysis and shows bond lengths (FIG. 1A) and angles (FIG. 1B) for the compound.
Figure 1B:
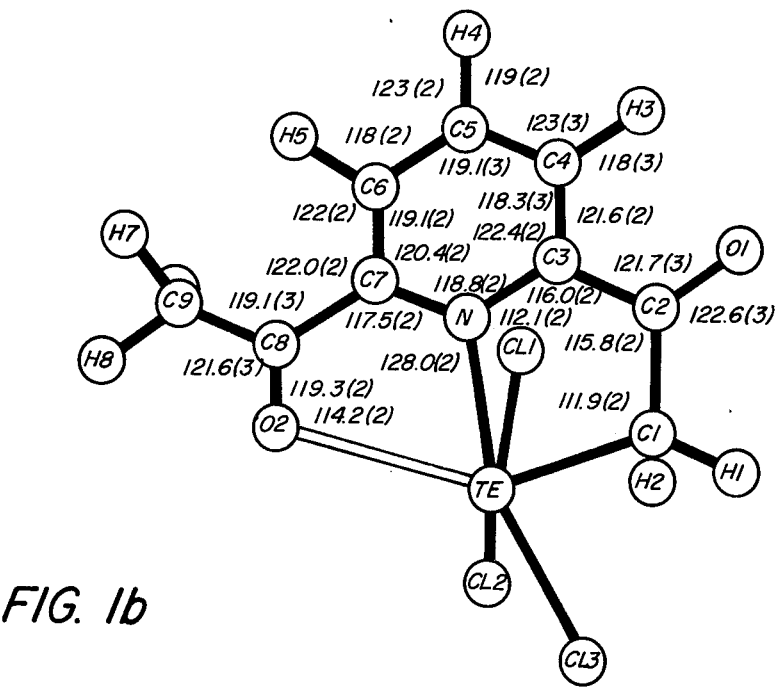

It is contemplated that there can be more than one group VA or VIA donor atom in the ligand coordinated to the Te(IV), i.e., Q can contain a second group VA or VIA donor atom. For example, in a compound of the invention, 2,6-diacetylpyridine (1-C) tellurium trichloride, it has been found that both the nitrogen in the pyridine ring and the oxygen in one of the carbonyl groups is coordinated to the Te(IV). The crystal structure of this compound is illustrated in FIG. 1 and can be represented by the formula:

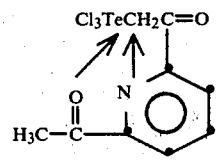

The carbon atom of the ligand need not be bound to the same Te(IV) atom that coordinates to the group VA or VIA donor atom. That is, intra (m=1), as well as inter (m>1), molecular coordination is contemplated. Thus, 2-acetylpyridine (1-C) tellurium trichloride can be present either in the form represented by:

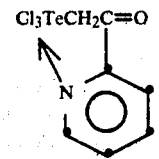

or in the form represented by:

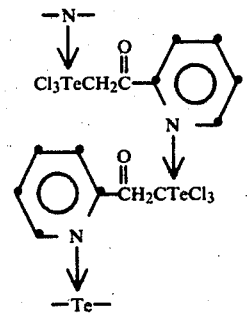

In the case of intermolecular coordination, compounds of the present invention are represented by the above general formula wherein D is coordinated to the tellurium of the next adjacent repeating unit and wherein m is an integer greater than 1.

In the general formula above, D is a radical incorporating 1 or 2 Lewis base functions, each function containing a group VA or VIA donor atom, such as N, O, S and the like and is coordinated with a tellurium atom of the compound. A number of these functional groups are known in the art and any may be a part of ligands which are useful herein. Typical examples of useful groups include amino, including substituted amino, cyano, hydroxyl, carbonyl, mercapto and heterocyclic groups containing O and/or N as hetero atoms, such as furan and pyridine, and the like. Whether these groups are coordinated to the Te(IV) can be readily determined by various physical methods which are well known in the art. Infrared spectroscopy is an especially useful and convenient method. The shift in the infrared spectrum of various groups due to coordination is known. For example, free 2,6-diacetylpyridine exhibits a single carbonyl stretching band at 1710 cm$^{-1}$, while two carbonyl stretching bands, one at 1696 cm$^{-1}$ and another at 1710 cm$^{-1}$, are exhibited in 2,6-diacetylpyridine (1-C) tellurium trichloride. This indicates coordination of one of the carbonyl functions to the Te(IV).

The Q in the formula above represents the atoms necessary to complete a 5- or 6-membered ring when taken together with the carbon and D which are bound to the tellurium(IV) atom (the tellurium atom itself thereby becomes one of the members in the ring wherein m is 1). The exact nature of these atoms is not critical and they can form, together with D and the carbon which are bound to Te(IV), a wide variety of ligands. In the case of intermolecular coordination (m>1), Q represents only the atoms linking C and D, and does not contribute to the completion of a 5- or 6-membered ring. Q can possess the same divalent groups in the case of intermolecular coordination as it represents for the intramolecular coordinated compound. Preferred linking groups useful in compounds wherein m is greater than 1 are alkylene, preferably containing from 1 to 6 carbon atoms, such as methylene, ethylene, propylene, hexylene and the like; and arylene containing from 6 to 12 carbon atoms, as well as phenylene, as well as substituted arylene and the like. Useful ligands include the following:

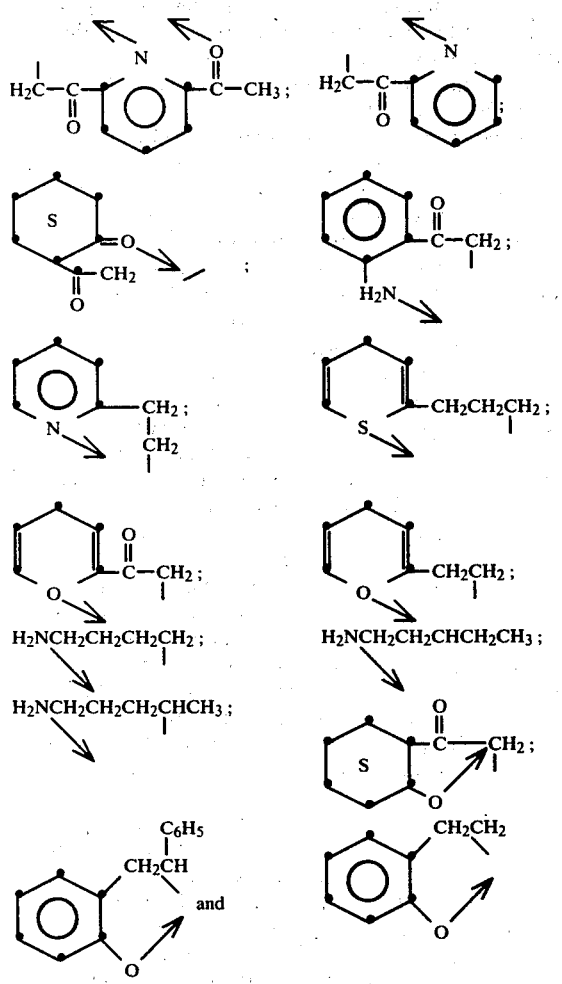

As illustrated above, $R_1$ and $R_2$ can be either hydrogen, alkyl or aryl, but are preferably both hydrogen. As used herein, alkyl is intended to include branched, straight-chain and cyclic alkyl, as well as substituted alkyl. Similarly, aryl is intended to be broadly construed to include substituted aryl and multiple-ring aryl. Typically, an alkyl group can have between 1 and 10 carbon atoms, and an aryl group can have between 6 and 12 carbon atoms.

The anion X is present simply to balance the charge of the compound. The particular anion is not critical. An extremely wide variety of anions are useful, including, but not limited to, halides, such as chloro, bromo, and iodo, which are preferred anions; ions which function like halides, such as $(NCO)^\ominus$, $(NCS)^\ominus$, $(NCSe)^\ominus$, $(NCTe)^\ominus$ and the like; hydroborate ions, such as $(BH_4)^\ominus$, $(B_3H_8)^\ominus$, $(B_9H_{14})^\ominus$, and the like; carboxylates, such as $(CH_3CO_2)^\ominus$, $(CF_3CO_2)^\ominus$, and the like; $(NO_2)^\ominus$; $(NO_3)^\ominus$; $(BF_4)^\ominus$; $B(C_6H_5)_4^\ominus$; $(ClO_4)^\ominus$; $(PF_6)^\ominus$ and the like.

Compounds of the present invention can be made by methods which are well known in the art for making organo tellurium(IV) compounds. Where the organic radical precursor contains an active hydrogen, the present compounds can be made by simply reacting $TeX_4$ with the organic radical precursor in solution. The solvent should be chosen so that the $TeX_4$ and the organic radical precursor are soluble therein. Typical useful solvents include chloroform, benzene, ethanol, methanol, toluene, methylene chloride, ethyl acetate and the like. Where the product is soluble in the solvent chosen for the reaction, the resulting product can be recovered by evaporation.

Generally, standard temperature and pressure can be used. The optimum reaction conditions will depend on such factors as the particular reactants, the desired reaction rate, reactant concentrations and the like. In some instances, therefore, it may be desirable to use other than standard temperature and pressure where convenient or in order to optimize results.

Compounds of the present invention which have been made by this general method include:

I. 2,6-diacetylpyridine (1-C) tellurium trichloride

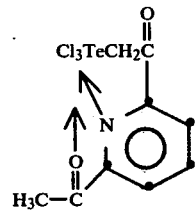

II. 2-acetylpyridine tellurium trichloride

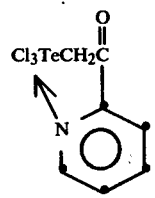

III. 2-acetylcyclohexanone tellurium trichloride

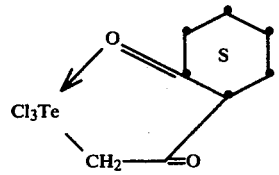

The compounds of the present invention can also be made by other methods well known in the art. A useful summary of these methods can be found in K. J. Irgolic, "The Organic Chemistry of Tellurium", Gordon and Breach Science Publishers, London, 1974. The formation of the compounds of this invention depends on the selection of the proper ligand, rather than the synthetic route. Briefly, the present compounds can be made by the reaction of $TeX_4$ with an organomercury compound; by the addition of $TeX_4$ across the carbon to carbon double bond of an olefin; or by the alkylation of a sodium telluride.

An important embodiment of the invention is an image-forming combination comprising (i) the described Te(IV) compound as an oxidizing agent, and (ii) a reducing agent. The image-forming combination can be in a solvent, thereby forming a physical developer solution. Alternatively, it can be coated on a suitable support, either alone or with other components to form an amplification element. Optionally, the image-forming combination can further comprise a binder to facilitate coating on a support. The image-forming combination can be activated by heating. The exact time and temperature of heating depends on the particular materials chosen, the degree of development desired, the particular material on which it is desired to deposit Te(0) and other factors. Usually, the image-forming combination will deposit tellurium when heated to a temperature within the range of about 75° C. to about 220° C., until a desired image is developed, typically within about 1 to about 90 seconds. The image-forming combination is preferably heated to a temperature within the range of about 100° C. to about 170° C. until the desired image is developed, such as within about 2 to about 60 seconds.

The heat-developable image-forming combination according to the invention can also comprise one or more other oxidizing agents than the described Te(IV) oxidizing agent, if desired. For example, the heat-developable materials according to the invention can contain a silver salt oxidizing agent, such as a silver salt of a long-chain fatty acid. Such silver salt oxidizing agents are typically resistant to darkening upon illumination. Typically useful silver salts of long-chain fatty acids are those containing about 17 to 30 carbon atoms. Compounds which are useful silver salt oxidizing agents include, for example, silver behenate, silver stearate, silver oleate, silver laurate, silver hydroxystearate, silver caprate, silver myristate and silver palmitate. Silver salts which are not silver salts of long-chain fatty acids can be also useful in combination with the described tellurium compounds. Such silver salt oxidizing agents include, for example, silver benzotriazole, silver benzoate, silver terephthalate, silver complexes and the like. Examples of other heavy metal salt oxidizing agents are gold stearate, mercury benhenate and gold behenate. Combinations of the described oxidizing agents can also be useful.

The described heat-developable image-forming combinations can contain a variety of organic reducing agents or inorganic reducing agents or combinations thereof, with organic reducing agents being preferred. Reducing agents which are especially useful are silver halide developing agents. Examples of useful reducing agents include phenolic reducing agents, such as polyhydroxybenzenes, including, for example, hydroquinone, alkyl-substituted hydroquinones, including tertiary butyl hydroquinone, methyl hydroquinone, 2,5-dimethylhydroquinone and 2,6-dimethylhydroquinone; catechols and pyrogallols; chlorosubstituted hydroquinones such as chlorohydroquinone or dichlorohydroquinone; alkoxy-substitued hydroquinones, such as methoxyhydroquinone or ethoxyhydroquinone; aminophenol reducing agents, such as 2,4-diaminophenols and methylaminophenols; ascorbic acid reducing agents, such as ascorbic acid, ascorbic acid ketals and ascorbic acid derivatives; hydroxylamine reducing agents; 3-pyrazolidone reducing agents, such as 1-phenyl-3-pyrazolidone and 4-methyl-4-hydroxymethyl-1-phenyl-3-pyrazolidone; reductone reducing agents, such as 2-hydroxy-5-methyl-3-piperidino-2-cyclopentenones; sulfonamidophenol reducing agents, such as the sulfonamidophenol reducing agents described in *Research Disclosure*, January 1973, pages 16 through 21; and the like. Combinations of reducing agents can be employed, if desired. Selection of an optimum reducing agent or reducing agent combination will depend upon such factors as processing conditions, desired image, other components of the imaging material and the like.

A range of concentration of reducing agent is useful in the described heat-developable image-forming combination according to the invention. The optimum concentration will depend upon such factors as the particular photographic composition, processing conditions, desired image and the like. Typically, a concentration of about 1.0 to about 100 moles of reducing agent per mole of described oxidizing agent or oxidizing agent combination is employed in the described image-forming combination. The preferred concentration is within the range of 1.0 to about 10 moles of reducing agent per mole of described oxidizing agent. A typical concentration of described reducing agent is, in a heat-developable image element, about 0.1 to about 1000 mg/ft$^2$ of support which corresponds to 0.01 to 100 mg/dm$^2$. An especially useful concentration of described reducing agent is, in a heat-developable image element, about 1 to 500 mg/ft$^2$ which corresponds to 0.1 to 50 mg/dm$^2$.

The heat-developable image-forming combination, according to the invention, can contain various colloids and polymers alone, or in combination, as vehicles and binding agents. Suitable materials can be hydrophobic or hydrophilic. They are transparent or translucent and include both naturally-occurring substances, such as protein, such as gelatin, gelatin derivatives, cellulose derivatives, polysaccharides, such as dextran, gum arabic and the like; and synthetic polymeric substances, such as water-soluble polyvinyl compounds, including poly(vinyl pyrrolidone), acrylamide polymers and the like. Other synthetic polymeric compounds which can be employed include dispersed vinyl compounds, such as in latex form, and particularly those which increase dimensional stability of photographic materials. Effective polymers include water-insoluble polymers of alkyl acrylates and methacrylates, acrylic acid, sulfoalkyl acrylates, methacrylates and those which have crosslinking sites which facilitate hardening or curing. Especially useful materials are high molecular weight materials and resins which are compatible with the described tellurium compounds, including poly(vinyl butyral), cellulose acetate butyrate, poly(methyl methacrylate), poly(vinylpyrrolidone), ethylcellulose, poly(styrene), poly(vinyl chloride), poly(isobutylene), butadiene-styrene copolymers, vinyl chloridevinyl acetate copolymers, copolymers of vinyl acetate, vinyl chloride and maleic acid and poly(vinyl alcohol). Combinations of the described colloids and polymers can also be used.

An element having a layer containing an imagewise distribution of physically developable catalyst can be physically developed by any of a wide variety of methods using the image-forming combination of the present invention. A suitable method is to simply immerse the element into a physical developer solution comprising the described Te(IV) complex and a reducing agent in a suitable solvent. Alternatively, the catalyst layer can be overcoated with a viscous physical developer solution containing the image-forming combination. In still another method, the catalyst layer can be contacted with a dry amplification element containing the image-forming combination of the invention.

Typically, nuclei of tellurium and of elements from groups VIII and IB of the periodic table such as silver, palladium and copper are catalytic for the deposition of Te(0) from the image-forming combination described herein. Any method of producing an imagewise distribution of these nuclei is useful. For example, the nuclei can be imagewise deposited by vacuum deposition. Alternatively, compounds which are capable of producing these nuclei may be imagewise reduced, such as by a photoreductant, to form the nuclei. Still another method is to expose photosensitive compounds of these metals to form the catalytic nuclei.

Many methods are known thereby positive catalytic images can be formed. For example, a photoreactive composition can be included in a layer comprising a uniform distribution of catalyst. Exposure of the photoreactive composition can release a material which inhibits the catalytic ability of the catalyst, thereby producing a positive catalytic image. In another method, a positive catalytic image can be formed by electrophotographically destroying the catalytic ability of a uniform distribution of catalyst. This process is described in commonly assigned copending Application Ser. No. 824,136, filed Aug. 8, 1977, entitled "Electrophotographic Elements and Processes" by Lelental and Light, now U.S. Pat. No. 4,113,484.

The following references relate to the described and other methods for producing an imagewise distribution of physically developable catalyst: U.S. Pat. Nos. 3,206,310; 3,291,608; 3,425,836; 3,600,185; 3,615,431; 3,637,388; 3,649,272; 3,933,496; 3,730,721; 3,719,490; 3,880,724; 3,860,500; 3,860,501; 3,859,092; and 3,700,448; British Pat. Nos. 1,308,431; 1,322,409 and 1,376,836; and *Research Disclosure* publications 13705 (September 1975); 15962 (July 1977); 15961 (July 1977); 15954 (July 1977) and 16235 (October 1977).

The elements containing the described image-forming combination can take a wide variety of forms. In one embodiment, an amplification element comprises a support having coated thereon an oxidation-reduction image-forming combination comprising (i) the described Te(IV) compound as an oxidizing agent, and (ii) a reducing agent. In another embodiment, a heat-developable photographic element comprises a support having coated thereon, in reactive association; (a) a photosensitive metal compound, and (b) an oxidation-reduction image-forming combination comprising (i) the described Te(IV) compound as an oxidizing agent, and (ii) a reducing agent.

As used herein, the term "reactive association" means that the reactive components are in the same layer and/or in an adjacent layer and/or in a layer that is separated by a layer or layers that is permeable to the reactive components and byproducts.

The support for the elements described herein can be a variety of support materials which can tolerate the processing temperatures employed. Typical supports include cellulose ester film; poly(vinyl acetal) film, poly(ethylene terephthalate) film, polycarbonate film and polyester film supports, as described in U.S. Pat. No. 3,634,089 of Hamb, issued Jan. 11, 1972, and U.S. Pat. No. 3,725,070 of Hamb et al, issued Apr. 3, 1973, and related films and resinous materials, as well as glass, paper, metal and the like. Typically, a flexible support is employed.

The support can be coated by various coating procedures known in the photographic art, including dip coating, air-knife coating, curtain coating or extrusion coating using hoppers, such as described in U.S. Pat. No. 2,681,294 of Beguin, issued June 15, 1954. If desired, two or more layers can be coated simultaneously, such as described in U.S. Pat. No. 2,761,791 of Russell, issued Sept. 4, 1956 and British Pat. No. 837,095.

The described components of the heat-developable elements according to the invention can be in any suitable location in the element which provides the desired image. One or more of the components can be in one or more layers of the element, preferably contiguous layers. For example, a certain percentage of the reducing agent, and/or other addenda, can be in a protective layer over the element.

The photosensitive metal compound can be any photosensitive metal salt or complex which provides the desired developable nuclei upon imagewise exposure. Typical metal compounds include salts and complexes of copper, palladium and silver. Useful metal compounds are described in the references cited above in relation to forming catalytic images. An especially useful photographic metal compound comprises photographic silver halide due to its high degree of photosensitivity. A typical concentration of photosensitive metal compound is from about 0.0001 to about 10.0 moles of photosensitive metal compound per mole of oxidizing agent in the oxidation-reduction image-forming combination. For example, a typically useful concentration range of photographic silver halide comprises about 0.001 to about 2.0 moles per mole of the described tellurium complex. Useful silver halide compositions and their method of manufacture are described, for example, in *Product Licensing Index*, Volume 92, December 1971, publication 9232, beginning on page 197. Other photosensitive metal compounds that provide physically developable nuclei which are useful include photosensitive chromium, iron, cobalt, nickel, copper, cadmium, selenium, palladium, silver, tin, tellurium, iridium, ruthenium, rhenium, manganese, platinum, rhodium, gold and lead compounds and combinations of these compounds.

Especially useful photosensitive metal compounds are selected from the group consisting of photosensitive silver, tellurium, palladium, copper and gold compounds. Examples of such compounds include: $Te(S_2P(OCH_3)_2)_2$; $K_2Pd(C_2O_4)_2$; $Pd(P(C_6H_5)_3)_2(C_2O_4)$; $[Cu(P(OCH_3)_3)_4]B(C_6H_5)_4$; $[Cu(P(OCH_3)_3)BH_3CN]_2$; $Cu(Sb(C_6H_5)_3)_3Cl$; and $[Cu(ethylenediamine)_2][B(C_6H_5)_4]_2$. Other photosensitive Pd complexes are described in U.S. Pat. Nos. 3,719,490; 4,046,569 and *Research Disclosure* 13705 (September 1975, B. F. Nellis). Other particularly useful Cu complexes are described in U.S. Pat. Nos. 3,859,092; 3,860,500; 3,860,501; 3,927,055 and 3,880,724.

It is desirable, in some cases, to employ a stabilizer or a stabilizer precursor in the described heat-developable materials according to the invention to improve post-processing stability. In some cases, the tellurium complexes themselves are stable after processing. However, in the case of photographic silver halide materials, it can be desired to stabilize the photographic silver halide after processing, in order to avoid post-processing printout. A variety of stabilizer or stabilizer precursors can be useful in the heat-developable photographic materials as described. These stabilizers or stabilizer precursors can be used alone or in combination. Typical useful stabilizers or stabilizer precursors include photolytically-activated polybrominated organic compounds, such as described in U.S. Pat. No. 3,874,946 of Costa et al, issued Apr. 1, 1975, and blocked stabilizer precursors, such as described in Belgian Pat. No. 768,071, issued July 30, 1971, and 4-aryl-1-carbamyl-2- tetrazoline-5-thione stabilizer precursors, such as described in U.S. Pat. No. 3,893,859 of Burness et al, issued July 8, 1975. Useful concentrations of stabilizer or stabilizer precursors can be determined by reference to the publications relating to these components.

It is, in some cases, useful to employ a so-called overcoat layer on the heat-developable elements to reduce fingerprinting and abrasion marks. The overcoat layer can be one or more of the described polymers which are also useful as binders or other polymeric materials which are compatible with the heat-developable layer and can tolerate the processing temperature employed.

The heat-developable materials can contain development modifiers that function as speed-increasing compounds, hardeners, antistatic layers, plasticizers and lubricants, coating aids, brighteners, spectral sensitizing dyes, absorbing and filter dyes, also as described in the above-referenced *Product Licensing Index*, Volume 92, December 1971, publication 9232, pages 107 through 110.

Development can also be effected using a diffusion transfer process. In one embodiment of such a process, a photosensitive element comprising a photosensitive metal salt, for example, a photosensitive salt of silver, palladium, tellurium or copper, is exposed in the usual manner and is then contacted with a receiving sheet comprising the described tellurium(IV) compound and a reducing agent. When the element and receiving sheet are in contact, heat is applied to promote diffusion of unexposed photosensitive metal salt from the element to the receiving sheet. Contact temperatures of from 45° C. to 200° C. are suitable. In the unexposed areas of the element, the metal salt migrates from the element to the receiving sheet, where it is reduced and catalyzes the reduction of the tellurium compound to tellurium metal by the reducing agent in the sheet to form a positive image on the receiving sheet.

In another embodiment of a diffusion transfer process, the photosensitive element comprises at least one photosensitive layer having permanently associated therewith a receiving layer. The photosensitive layer comprises a photosensitive metal salt and the receiving layer comprises the described tellurium(IV) compound and a reducing agent according to the invention. The element is exposed in the usual manner and is then heated at about 75° C. to 250° C. to promote diffusion of unexposed photosensitive metal salt to the receiving layer. In the unexposed areas of the photosensitive layer, the metal salt diffuses from the layer to the receiving layer where it is reduced and acts as a catalyst to form a positive image on the receiving layer.

Some of the Te(IV) compounds described herein are photosensitive. By photosensitive, it is meant that these compounds form physically developable tellurium nuclei when exposed to about $10^{-8}$ ergs of radiation per square centimeter or less. After imagewise exposure, a photosensitive element, having coated thereon the described Te(IV) compound, can be physically developed by known methods. Physical development compositions and processes are described, for example, in U.S. Pat. Nos. 2,223,525; 3,253,923; 3,390,998; 3,576,631; 3,578,449; 3,591,609; 3,650,748; 3,512,972; 3,893,857; 3,935,013 and 4,042,392; British Pat. No. 1,125,645; *Research Disclosure* 15631; Hornsby, *Basic Photographic Chemistry*, (1956) 66; and Mees and James, *The Theory of the Photographic Process*, 3rd Edition (1966), pages 329 through 331. A useful photographic element is an element as described above wherein the photosensitive metal compound is the described Te(IV) compound.

The following examples are presented to illustrate but not limit the invention.

EXAMPLE 1—Synthesis of 2,6-diacetylpyridine (1-C) tellurium trichloride

To a solution of $TeCl_4$ (25 g, 92.8 mmoles) in 400 ml of $CHCl_3$, under an argon atmosphere, was added 15.2 g (93 mmoles) of 2,6-diacetylpyridine. The reaction solution, which did not evolve HCl at room temperature, was refluxed for 24 hours under the inert atmosphere, then cooled to room temperature and diluted with 1 liter of ethyl ether to give a brown precipitate. This crude product was filtered, washed with ether and air dried (27.7 g [59 percent based on $Cl_3Te(C_9H_8NO_2)$]). Recrystallization of this crude product from 1300 ml of hot $CH_2Cl_2$ (and activated carbon) gave 12.6 g of bright yellow crystals (overall yield=33.5 percent; m.p. darkens above 165° C., 205° C. gives murky black melt). Presence of the title compound was confirmed by elemental analysis, infrared spectral analysis and x-ray crystal structure analysis.

The infrared spectrum of the title compound (mineral oil mull) exhibits two carbonyl stretching bands (1696 and 1710 cm$^{-1}$; free 2,6-diacetylpyridine exhibits one band at 1710 cm$^{-1}$). Evidence for coordination of the ring nitrogen to tellurium is also obtained from the infrared spectrum. The ring breathing band is shifted from 997 cm$^{-1}$ in 2,6-diacetylpyridine to 1013 cm$^{-1}$ in the Te compound. Such a shift to higher energy in metal compounds of pyridine derivatives indicates coordination to the pyridyl nitrogen. Other infrared absorptions also support the coordination of the ring nitrogen to tellurium:

(a) the 2-ring vibrations at 1410 and 1578 cm$^{-1}$ are shifted to higher energy in the Te compound (i.e., 1418 and 1592 cm$^{-1}$);

(b) the weak band at 1568 cm$^{-1}$ in free 2,6-diacetylpyridine is reinforced in the Te compound.

EXAMPLE 2—X-ray crystal structure analysis of 2,6-diacetylpyridine-(1-C) tellurium trichloride Large, yellow, acicular (c) crystals of the compound of Example 1 were obtained by recrystallization from a hot methylene chloride/ether solution. A crystal 0.28*0.28* 0.43 mm was cemented onto a thin glass rod and used for intensity data collection at 25°±1° C. on an automatic Picker four-circle goniostat with Zr-filtered Mo radiation. Systematic absences in precession photographs established the space group as $P2_1/a$. The crystal data for the sample is listed below:

| Cell parameters | | |
|---|---|---|
| | a(A) | 13.662(6) |
| | b | 10.900(6) |
| | c | 8.726(6) |
| | β(deg) | 102.62(1) |
| | V(A3) | 1268(1) |
| | Z | 4 |
| $D_{calc}$ g cm$^{-3}$ | | 2.075 |
| $D_{obs}$, flotation | | 211 |
| Linear absorption coeff, cm$^{-1}$ (MoKa) | | 29.8 |
| Absent spectra | | h0l, h odd |
| | | 0k0, k odd |
| Space group | | $P2_1/a$ |
| M.W. | | 396.13 |
| F(000) | | 752 |

The procedures used for lattice constant refinement data collection and data reduction are described in D. L. Smith and H. R. Luss, Photog. Sci. Eng. 20, 184 (1976). The structure was solved by the heavy-atom method from three-dimensional Patterson and Fourier maps. Refinement was by full matrix least squares using program ORFLS (W. R. Busing et al, Report ORNL TM-305, Oak Ridge National Laboratory [1962]). Details of this program are described in H. R. Luss and D. L. Smith, Acta., Cryst., 29B, 998 (1973). Atomic scattering factors for all atoms and the anomalous dispersion corrections for Te and chlorine were obtained from *International Tables for X-Ray Crystallography* ("International Tables for X-Ray Crystallography", Volume IV, Chapter 11, Kynch Press, Birmingham, England).

FIG. 1 shows a stereographic view (K. Johnson, ORTEP-II, Report ORNL-3794, 2nd revision, Oak Ridge National Laboratory [1971]) of the molecule with bond lengths and atomic labeling. The coordination number of tellurium is six, although the Te-O bond is considerably longer than the sum of covalent radii. This Te-O bond is represented by the open bond. The coordination geometry can be described as pentagonal bipyramidal with the lone pair of electrons becoming stereochemically active, occupying a position in the coordination polyhydron between 02 and chlorine 3. The Te-C bond length is comparable to those commonly found for Te(IV)-$C_{sp}3$ in such structures as 1,1-dichlorotelluracyclohexane-3,5-dione (C. L. Raston et al, J. Chem. Soc. [Dalton], 2307 [1976].

EXAMPLE 3—The use of 2,6-diacetylpyridine-(1-C) tellurium trichloride as an oxidant in an amplification element A dry tellurium physical development element was prepared by coating (8 mil wet thickness) on paper support a solution of 100 mg t-butylhydroquinone and 85.9 mg of the tellurium compound described in Example 1 in 19 ml of a 5 percent solution of poly(vinylbutyral) (Butvar ® B-76, available from Monsanto Company) in methylene chloride-1,1,2-trichloroethone-methanol (7:3:5). The element was stable to aerial hydrolysis for at least 6 months. Lamination of this dry tellurium physical development element with palladium nuclei, vacuum deposited in step tablet distribution, at 150° C. for 10 seconds, resulted in selective amplificatiion of the palladium nuclei down to a coverage of $1 \times 10^{14}$ atoms/cm$^2$.

EXAMPLE 4—Synthesis of 2-acetylpyridine (1-C) tellurium trichloride

To a solution of 22.5 g (187 mmoles) 2-acetylpyridine dissolved in 350 ml of purified chloroform was added 25 g (93 mmoles) of TeCl$_4$. The reaction solution was refluxed for 10 hours under an argon atmosphere, a red-brown solid forming. The reaction solution was filtered and the solid washed with chloroform and air dried to give 32 g of red-brown solid (m.p.: gums 85° C., murky red melt by 110° C.). This product is insoluble in CHCl$_3$, CH$_2$Cl$_2$, acetone and benzene, but soluble in dimethylformamide. Elemental analysis confirmed the presence of the title compound.

The infrared spectrum of the title compound indicates that the pyridine nitrogen is coordinated to the tellurium (i.e., ring breathing band shifts from 992 cm$^{-1}$ in the free pyridine compound to 1012 cm$^{-1}$ in the organotellurium compound). The solubility properties of this product, however, suggest that the N is coordinated in an intermolecular bonding mode, rather than in in intramolecular mode, as in the 2,6-diacetylpyridine analog.

EXAMPLE 5—Synthesis of 2-acetylcyclohexanone (1-C) tellurium trichloride

2-Acetylcyclohexanone (14.02 g, 0.1 mole) was added to a suspension of tellurium tetrachloride (13.45 g, 0.05 mole) in 150 ml of chloroform. The solution was heated at reflux for 30 minutes, cooled to room temperature and filtered. The volume of the filtrate was reduced to 100 ml and 150 ml of ether was added. Cooling overnight yielded a cream-colored solid which was filtered and dried. Concentration of the mother liquor and cooling yielded another 1.1 g of product. Total yield: 5.6 g (30 percent); m.p. darkens over 105° C., black melt 129° to 131° C. The title compound was confirmed by elemental analysis.

The shift of the carbonyl stretching frequency for this compound (i.e., broad band centered at 1605 cm$^{-1}$ in free ligand versus 2 resolved bands at 1570 and 1540 cm$^{-1}$ in the organotellurium compound) indicates coordination of a carbonyl function.

The invention has been described in detail with particular reference to preferred embodiments thereof, but it will be understood that variations and modifications can be effected within the spirit and scope of the invention.

What is claimed is:

1. An image-forming combination comprising (i) a tellurium(IV) compound represented by the formula:

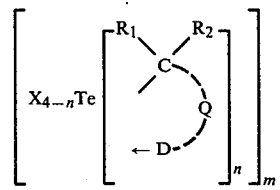

wherein:

D is coordinated to a Te atom of the compound and comprises a radical incorporating one or two Lewis base functions, each function containing a group VA or VIA donor atom;

Q represents the atoms necessary to complete a 5- or 6-membered ring when taken together with C, D and Te when m is 1 and represents the atoms linking C and D when m is greater than 1;

R$_1$ and R$_2$ are independently selected from the group consisting of hydrogen, alkyl and aryl;

X is an anion;

n is 1; and m is an integer from 1 to 500;

as an oxidizing agent, and (ii) a reducing agent.

2. An image-forming combination according to claim 1 further comprising a binder.

3. An image-forming combination according to claim 1 further comprising a solvent.

4. An image-forming combination according to claim 1 wherein R$_1$ and R$_2$ are hydrogen and X is halogen.

5. An image-forming combination according to claim 1 wherein D is selected from the group consisting of amino, cyano, hydroxyl, carbonyl, heterocyclic and mercapto.

6. An image-forming combination according to claim 1 wherein Q, when taken together with C and D, forms a ligand selected from the group consisting of:
2,6-diacetylpyridine;
2-acetylpyridine; and
2-acetylcyclohexanone.

7. An image-forming combination according to claim 1 wherein said tellurium(IV) compound is selected from the group consisting of:
2,6-diacetylpyridine (1-C) tellurium trichloride;
2-acetylpyridine (1-C) tellurium trichloride; and
2-acetylcyclohexanone tellurium trichloride.

8. An amplification element comprising a support having coated thereon an image-forming combination comprising (i) a tellurium(IV) compound represented by the formula:

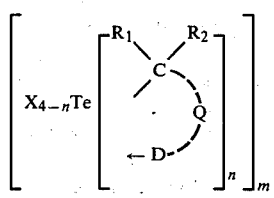

wherein:
D is coordinated to a Te atom of the compound and comprises a radical incorporating one or two Lewis base functions, each function containing a group VA or VIA donor atom;
Q represents the atoms necessary to complete a 5- or 6-membered ring when taken together with C, D and Te when m is 1 and represents the atoms linking C and D when m is greater than 1;
$R_1$ and $R_2$ are independently selected from the group consisting of hydrogen, alkyl and aryl;
X is an anion;
n is 1; and
m is an integer from 1 to 500,
as an oxidizing agent, and (ii) a reducing agent.

9. An amplification element according to claim 8 wherein said image-forming combination is in a binder.

10. An amplification element according to claim 8 wherein said reducing agent is a silver halide developing agent.

11. An amplification element according to claim 8 wherein $R_1$ and $R_2$ are hydrogen and X is halogen.

12. An amplification element according to claim 8 wherein D is selected from the group consisting of amino, cyano, hydroxyl, carbonyl, heterocyclic and mercapto.

13. An amplification element according to claim 8 wherein Q, when taken together with C and D, forms a ligand selected from the group consisting of:
2,6-diacetylpyridine;
2-acetylpyridine; and
2-acetylcyclohexanone.

14. An amplification element according to claim 8 wherein said tellurium(IV) compound is selected from the group consisting of:
2,6-diacetylpyridine (1-C) tellurium trichloride;
2-acetylpyridine (1-C) tellurium trichloride; and
2-acetylcyclohexanone tellurium trichloride.

15. A photothermographic element comprising a support having coated thereon, in reactive association, (a) a photosensitive metal compound, and (b) an image-forming combination comprising (i) a tellurium(IV) compound represented by the formula:

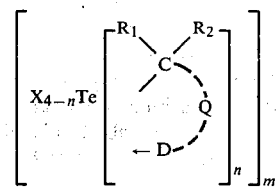

wherein:
D is coordinated to a Te atom of the compound and comprises a radical incorporating one or two Lewis base functions, each function containing a group VA or VIA donor atom;
Q represents the atoms necessary to complete a 5- or 6-membered ring when taken together with C, D and Te when m is 1 and represents the atoms linking C and D when m is greater then 1;
$R_1$ and $R_2$ are independently selected from the group consisting of hydrogen, alkyl and aryl;
X is an anion;
n is 1; and
m is an integer from 1 to 500,
as an oxidizing agent, and (ii) a reducing agent.

16. A photothermographic element according to claim 15 wherein said photosensitive metal compound is selected from the group consisting of silver, tellurium, palladium, copper and gold compounds.

17. A photothermographic element according to claim 16 wherein said photosensitive metal compound is a silver halide.

18. A photothermographic element according to claim 15 wherein said reducing agent is a silver halide developing agent.

19. A photothermographic element according to claim 15 wherein said photosensitive metal compound and said image-forming combination are in a binder.

20. A photothermographic element according to claim 15 wherein $R_1$ and $R_2$ are hydrogen and X is halogen.

21. A photothermographic element according to claim 15 wherein D is selected from the group consisting of amino, cyano, hydroxyl, carbonyl, heterocyclic and mercapto.

22. A photothermographic element according to claim 15 wherein Q, when taken together with C and D, forms a ligand selected from the group consisting of:
2,6-diacetylpyridine;
2-acetylpyridine; and
2-acetylcyclohexanone.

23. A photothermographic element according to claim 15 wherein said tellurium(IV) compound is selected from the group consisting of:
2,6-diacetylpyridine (1-C) tellurium trichloride;
2-acetylpyridine (1-C) tellurium trichloride; and
2-acetylcyclohexanone tellurium trichloride.

24. A process for forming an image comprising the step of contacting an imagewise distribution of physically developable catalyst with an image-forming combination comprising (i) a tellurium(IV) compound represented by the formula:

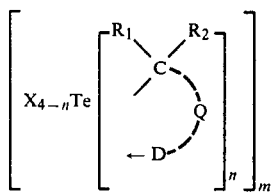

wherein:
- D is coordinated to a Te atom of the compound and comprises a radical incorporating one or two Lewis base functions, each function containing a group VA or VIA donor atom;
- Q represents the atoms necessary to complete a 5- or 6-membered ring when taken together with C, D and Te when m is 1 and represents the atoms linking C and D when m is greater than 1;
- $R_1$ and $R_2$ are independently selected from the group consisting of hydrogen, alkyl and aryl;
- X is an anion;
- n is 1; and
- m is an integer from 1 to 500, as an oxidizing agent, and (ii) a reducing agent.

25. A process for forming an image according to claim 24 further comprising the step of heating said image-forming combination in contact with said catalyst.

26. In a process for forming an image comprising the steps of:
(1) imagewise exposing a photosensitive layer comprising a photographic metal salt; and
(2) diffusing unexposed photographic metal salt from said photosensitive layer into a developer layer comprising an image-forming combination where said unexposed salt is reduced and catalyzes an image-forming reaction, thereby forming a positive image in said developer layer, the improvement wherein said image-forming combination comprises (i) a tellurium(IV) compound represented by the formula:

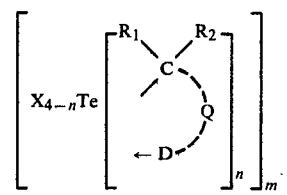

wherein:
- D is coordinated to a Te atom of the compound and comprises a radical incorporating one or two Lewis base functions, each function containing a group VA or VIA donor atom;
- Q represents the atoms necessary to complete a 5- or 6-membered ring when taken together with C, D and Te when m is 1 and represents the atoms linking C and D when m is greater than 1;
- $R_1$ and $R_2$ are independently selected from the group consisting of hydrogen, alkyl and aryl;
- X is an anion;
- n is 1; and
- m is an integer from 1 to 500, as an oxidizing agent, and (ii) a reducing agent.

* * * * *